United States Patent
Vedrine

(10) Patent No.: US 9,174,010 B2
(45) Date of Patent: Nov. 3, 2015

(54) SPRAYER, IN PARTICULAR FOR MEDICAL USE

(75) Inventor: Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1256 days.

(21) Appl. No.: 12/867,920

(22) PCT Filed: Feb. 2, 2009

(86) PCT No.: PCT/IB2009/050400
§ 371 (c)(1),
(2), (4) Date: Nov. 9, 2010

(87) PCT Pub. No.: WO2009/104106
PCT Pub. Date: Aug. 27, 2009

(65) Prior Publication Data
US 2011/0049265 A1    Mar. 3, 2011

(30) Foreign Application Priority Data

Feb. 19, 2008   (FR) ...................................... 08 00869

(51) Int. Cl.
*B05B 11/00* (2006.01)
*A61M 11/00* (2006.01)
(Continued)

(52) U.S. Cl.
CPC .............. *A61M 11/00* (2013.01); *A61M 11/007* (2014.02); *A61M 15/0025* (2014.02); *B05B 11/0027* (2013.01); *B65D 41/3409* (2013.01); *Y10T 29/49945* (2015.01)

(58) Field of Classification Search
CPC .. B05B 11/00; B05B 11/0008; B05B 11/001; B05B 11/0027; B65D 41/32; B65D 47/2062; B65D 41/3409; B65D 1/0238; B65D 51/20; B65D 17/06; B65D 47/10; B65D 2102/003; B65D 2101/0023; A61M 11/00; A61M 11/007; A61M 15/0025; Y10T 29/49945
USPC ......... 222/153.05, 153, 420, 421, 498, 541.1, 222/541.4, 541.6, 562, 153.1, 153.09; 239/302, 320; 215/250, 253, 256, 258, 215/252; 220/276, 266, 265
See application file for complete search history.

(56) References Cited

U.S. PATENT DOCUMENTS 4,344,573 A * 8/1982 De Felice ...................... 239/320
4,503,856 A * 3/1985 Cornell et al. ................ 606/182
(Continued)

FOREIGN PATENT DOCUMENTS

JP    2001-079089 A    3/2001

*Primary Examiner* — Justin Jonaitis
*Assistant Examiner* — Juan C Barrera
(74) *Attorney, Agent, or Firm* — The Webb Law Firm

(57) ABSTRACT

A sprayer includes a container of product to be sprayed, provided with a delivery opening for this product, and a spraying assembly. The spraying assembly is in fluid communication with the delivery opening and is securable onto the container by insertion about a mounting axis. The spraying assembly includes a sprayer body delimiting a proximal area conformed so as to be securable to the container, and includes a distal wall, transverse to the mounting axis, in which a spraying aperture is arranged, and a cap intended to be mounted on the sprayer body. The cap includes a wall transverse to the mounting axis, which is sufficiently rigid so as to bear, without substantial damaging, a force from 50 to 100 N necessary to secure the sprayer body to the container and thus to enable the transmission to the sprayer body of this force.

14 Claims, 3 Drawing Sheets

(51) Int. Cl.
  *A61M 15/00* (2006.01)
  *B65D 41/34* (2006.01)

(56) References Cited

U.S. PATENT DOCUMENTS 4,667,837 A * 5/1987 Vitello et al. ................. 215/228
4,746,035 A * 5/1988 Anderson et al. ......... 222/153.06
5,601,077 A * 2/1997 Imbert ..................... 128/200.14
5,785,691 A * 7/1998 Vetter et al. .................... 604/187
6,491,665 B1 * 12/2002 Vetter et al. .................... 604/181
6,626,379 B1 * 9/2003 Ritsche et al. ................ 239/337
7,044,125 B2 * 5/2006 Vedrine et al. ........... 128/200.19
2003/0111552 A1 * 6/2003 Vedrine et al. ................ 239/329

* cited by examiner

SPRAYER, IN PARTICULAR FOR MEDICAL USE

The invention relates to a sprayer, in particular for medical use. It also relates to a process for making this sprayer.

It is known to make a sprayer for medical use by assembling a spraying assembly on the product delivery opening of a container containing the medical product to spray, this container being in particular a syringe body. Reference can be made in this respect to the document U.S. Pat. No. 5,601,077.

As implemented, the spraying assembly according to this prior document includes an external part and an internal part placed inside the external part. The external part forms a distal chamber intended to receive the internal part and a proximal area allowing to secure the spraying assembly on the product delivery tip (particularly the tip of a syringe). At the distal end, the external part forms a transverse wall in which the spraying aperture is arranged. The internal part includes a distal end resting against the distal transverse wall of the external part and a proximal circumferential skirt radially deformable. In a state of non deformation, the skirt comes in contact with the peripheral inner wall of the external part, and, under the pressure of the liquid to be sprayed, collapses radially toward the interior to allow the liquid product to flow, the skirt thus forming a non-return valve preventing the backward flow of the liquid to the syringe. Once the external part is secured on the delivery tip of the syringe, it is then equipped with a protective cap made of a rubber or elastomer type flexible material, which is fixed on the external part.

In U.S. Pat. No. 5,601,077 as in this application, the distal end of a component or of a device means the end furthest away from the hand of the user and the proximal end means the end closest to the hand of the user. Similarly, in this application, the terms "in the distal direction" and "distally" mean in the direction of the injection, and the terms "in the proximal direction" and "proximally" mean in the direction opposite to the direction of injection.

The spraying assembly according to this document presents several drawbacks.

Firstly, it implies two assembly operations, one for the assembly of the external part equipped with the internal part to the syringe body and another one to install the protective cap. These two operations have an important effect on the complexity and the cost of the manufacturing of the sprayer.

The manufacturing constraints of this sprayer also induce an important variability of the positioning of the spraying assembly with respect to the syringe body. This variability implies a large dead volume, which leads to the need for an additional quantity of product to fill the syringe, and therefore results in an additional expense. This variability also results in a risk of variation of the volume of the amount to spray.

This sprayer moreover makes the presence of a protective cap necessary, tightly engaged on the whole distal part of the external part and inducing a risk of stagnation of the product between the external part and the protective cap.

Moreover this sprayer does not exclude the presence of air between the external part and the internal part after filling, which also affects the volume of the amount of delivered product.

Moreover, the removal of the protective cap may not be very easy to achieve.

Lastly, the sprayer is not tamper-evident, i.e. the cap can be removed and reinstalled without evidence.

The purpose of the present invention is to overcome all of these drawbacks.

The document WO 03/077975 discloses a nasal spray system in which the connection of the spray tip to the syringe is done by the user. No solution to the drawbacks mentioned above is disclosed by this document.

The document CA 2,492,255 discloses a cap of a container which sole function is covering and sealing the delivery opening. No solution to the drawbacks mentioned above is disclosed by this document.

The document U.S. Pat. No. 4,746,035 discloses a closure cap that is threaded onto a liquid container and is used for mounting the dispenser onto this container, the neck of the container being threaded in the same way. The sole function of the cap is covering and protecting the plunger head. Here again, no solution to the drawbacks mentioned above is disclosed by this document.

The document EP 0 636 421 does not provide any solution to the drawbacks mentioned above.

The main object of the invention is thus to provide a sprayer consisting of a spraying assembly and of a container containing the medical product to be sprayed, which can be assembled to one another with only one assembly operation.

Another object of the invention is to provide a sprayer having a reduced variability of the positioning of the spraying assembly with respect to the container.

Still another object of the invention is to provide a perfectly tight sprayer.

Still another object of the invention is to provide sprayer with a lower dead volume.

An additional object of the invention is to provide a sprayer that is easy to use and is tamper-evident.

The sprayer of the present invention includes, in a known way per se, a container of product to be sprayed, provided with a delivery opening of this product, and a spraying assembly, said spraying assembly being in fluid communication with this delivery opening and being securable onto this container by insertion about a mounting axis, this spraying assembly including a sprayer body delimiting a proximal area conformed so as to be securable to said container, and including a distal wall, transverse to said mounting axis, in which a spraying aperture is arranged, and a cap intended to be mounted on the sprayer body.

According to the invention, the cap includes a wall transverse to said mounting axis, being sufficiently rigid so as to bear without substantial damaging a force from 50 to 100 N necessary to secure this sprayer body to said container and thus to enable the transmission to said sprayer body of this force.

Thus, the rigidity of the material constituting said transverse wall of the cap is such that it allows the exercise on the cap of the force necessary for securing the sprayer body onto the container. In practice, that means that this material must be capable to bear a force from 50 to 100 N without substantial damaging, which excludes any material of the rubber or elastomer type; this material can be a current synthetic material, in particular a polypropylene.

The spraying assembly can thus be assembled to the container by only one assembly operation, which makes it possible to decrease the variability of the positioning of the spraying assembly with respect to the container.

The invention thus overcomes essential drawbacks of the prior technique.

Preferably, said transverse wall of the cap comes, in the mounted position of the cap on the sprayer body, in the immediate vicinity of said distal transverse wall of the sprayer body so as to eliminate or reduce any play between the cap with respect to the sprayer body.

Preferably, said transverse wall of the cap covers the spraying aperture and includes at least one sealing element at its area covering said spraying aperture, this sealing element making it possible to sealingly close the spraying aperture.

A sealing of this spraying aperture with respect to the cap is thus ensured.

According to another embodiment, this sealing element is placed around said spraying aperture; in particular it may have an annular form.

Preferably, the sprayer body and the cap are forming complementary engaging surfaces making it possible, when they are engaged, to axially limit the movement of the cap with respect to the sprayer body in said assembly position of this cap on this sprayer body.

Thus, in this assembled position, the cap and the sprayer body are assembled one with the other, forming a single unit, with limited axial mobility of the cap with respect to the sprayer body. This eases the implementation of the process of assembly of the spraying assembly to the container.

Preferably, in this case, the sprayer body forms a planar surface perpendicular to its longitudinal axis, and the cap forms an inwardly projecting edge able to rest against this planar surface.

The sprayer body and the cap can in particular be formed so that said edge can snap beyond said planar surface. The said sprayer body and cap could also be secured by gluing, crimping, hatching, or any appropriate securing technique.

Preferably, the cap consists in at least two coaxial parts connected one to the other by breakable bridges; one of these two parts is proximal and is intended to be secured to said sprayer body; the other part is distal and is intended to be withdrawn at the moment of the use of the sprayer, by rupture of said bridges.

These breakable bridges thus make the sprayer tamper-evident.

Said proximal part of the cap can in particular be maintained with respect to said sprayer body by means of the above mentioned complementary engaging surfaces which this sprayer body and the cap include.

According to a preferred embodiment of these complementary engaging surfaces,
  the container is a syringe body forming a shoulder at its connection area to the delivery opening;
  the above-mentioned planar surface of the sprayer body is arranged at the proximal end of this sprayer body;
  the above-mentioned inwardly projecting edge of the cap is arranged at the proximal end of this cap;
  the mounted position of the sprayer body is such that in the mounted position of this sprayer body on the container, said planar surface and said shoulder delimit between them a groove adjusted to the thickness of said edge, so that this edge can be received in this groove with minimal axial play.

Thanks to this axial play limitation, said proximal part of the cap is, after rupture of said bridges, axially maintained with respect to the remainder of the sprayer.

The rupture of the breakable bridges could be carried out by flexion or rotation of said distal part of the cap with respect to the proximal part of this cap. Preferably, however, the sprayer body and the cap are mutually dimensioned so that there exists, in the mounted position, a space between this sprayer body and this cap, this space being such that it allows the exercise of a transverse or rotational force on the distal part of the cap, making it possible to exert stresses on the breakable bridges in order to help to break these bridges.

The sprayer according to the invention can include an internal part placed in a distal chamber which said sprayer body delimits, this internal part having a length such that, in the mounted position, its distal end comes in the immediate vicinity of said distal transverse wall of the sprayer body while its proximal end comes in the immediate vicinity of the delivery opening.

These immediate proximities are made possible by the reduction of variability permitted by the invention and also contribute to this reduction of variability, the internal part being able to act as a spacer when the mounted position of the spraying assembly on the container is reached. The resting of this internal part against the transverse distal wall of the sprayer body allows the sealing of the sprayer and makes it possible moreover to reduce the dead volume of product in the chamber formed by the sprayer body.

Preferably, the internal part includes:
  a proximal portion dimensioned to be received in an adjusted manner in the part of said chamber intended to receive it, this proximal portion delimiting an internal proximal conduit for the flowing of the product to be sprayed;
  a distal portion intended, in the mounted position, to come against the internal surface of said distal transverse wall of the sprayer body, and dimensioned to delimit, between it and the wall of said chamber intended to receive it, at least one distal conduit for the flowing of the product to be sprayed, and
  an intermediate portion between this proximal portion and this distal portion, in which is arranged at least one transverse opening making it possible to put in communication said proximal conduit of said proximal portion and said distal conduit.

The internal part thus formed makes it possible to contribute to reduce the dead volume of product, and has moreover the advantage of being able to be moulded in only one part, by means of a simple mould, deprived of slides.

The sprayer body can include an assembly area at the level of said chamber and said internal part can form a complementary assembly area intended to cooperate with this assembly area to carry out the assembly of this sprayer body and this internal part. Said assembly area can be a groove arranged in the sprayer body and said complementary assembly area can be an annular rib intended to be retained in said groove; it could also be a recess or a stop, said internal part then including a projection or a complementary stop.

The movement of the internal part with respect to the sprayer body during its assembly can thus be axially limited, which eases the implementation of the manufacturing process of the sprayer according to the invention.

The distal conduit for the flowing of the product includes, as known per se, a cylindrical chamber in which emerge tangential conduits. This chamber and/or these conduits can be arranged in said distal transverse wall of the sprayer body or in the internal part.

The process according to the invention, for making the sprayer described above, comprises the following steps:
  mounting the cap on the sprayer body of the spraying assembly before mounting the sprayer body on the container, and
  exerting said force on said wall of said cap so as to enable the mounting of the spraying assembly onto the container.

The invention will be readily understood, and other characteristics and advantages thereof will appear, in reference to the annexed diagrammatic drawing, representing, as non-restrictive example, a preferred embodiment of the sprayer that it concerns.

Figure 2:
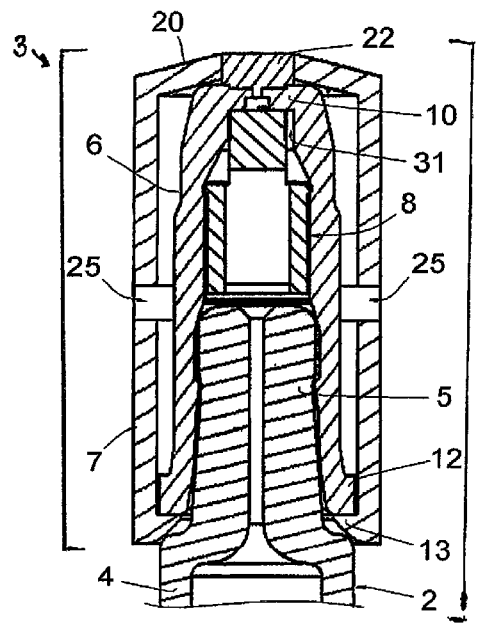
FIG. 2 is a view similar to FIG. 1, after assembly of these parts.
Figure 3:
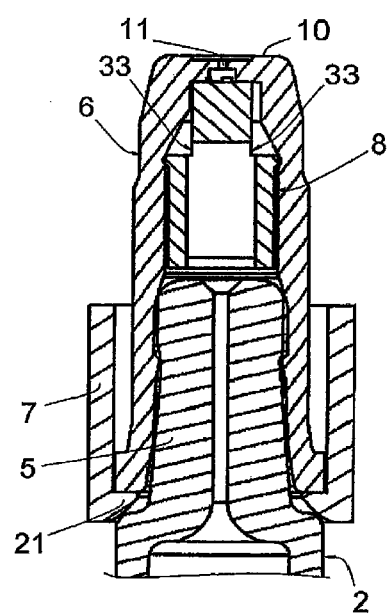
FIG. 3 is a view similar to FIG. 2, after removal of a separable part comprised by a part forming a protective cap.

FIG. 2 shows a sprayer 1 comprising a container 2 (partially shown), which contains the product to be sprayed, and a spraying assembly 3 designed to be connected to the container 2. In the illustrated example, the container 2 is a syringe body 4 without a needle, in glass, forming a tip 5 for delivering the product.

Figure 1:
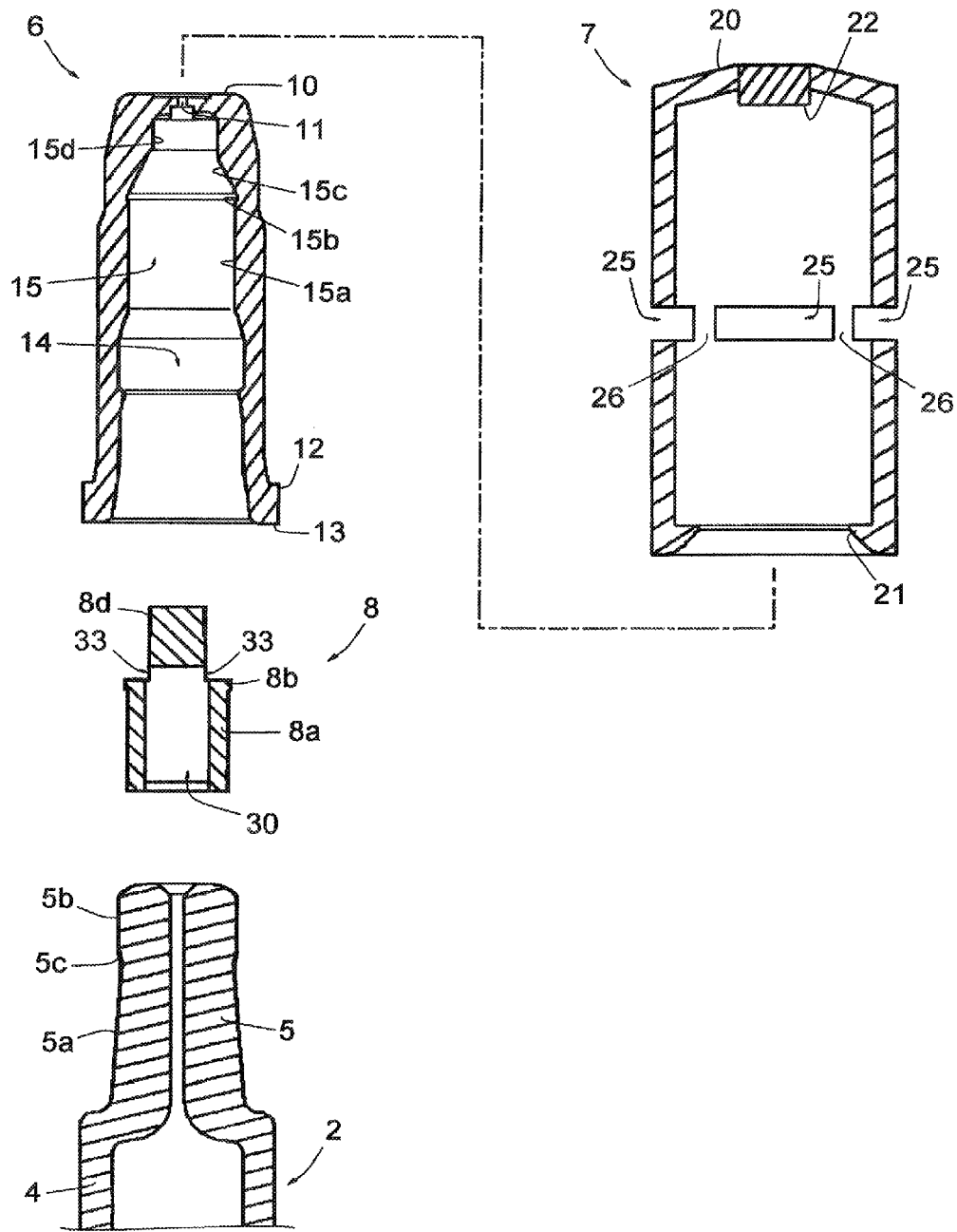
FIG. 1 is a side view, in longitudinal cross-section, of various parts comprised by this sprayer, before assembly.

The container 2 itself is known and therefore will not be described in detail. In reference to FIG. 1, one can see that the tip 5 comprises a conical proximal part 5a, a cylindrical distal part 5b and a slight shoulder 5c separating these two parts 5a, 5b, from the proximal side.

The sprayer assembly 3 comprises three parts 6, 7, 8, namely a sprayer body 6, a cap 7 and an internal part 8.

The body 6 is shaped like a bush open at one end and comprises, at its other end, a transverse wall 10 in which a sprayer aperture 11 is arranged. This body 6 may in particular be made in polypropylene.

The peripheral wall of this body 6 is generally slightly conical, and its cross-section decreases in the distal direction.

At its open end, the body 6 comprises a flange 12 defining an external shoulder 13 from the proximal side. From this open end, the body 6 inwardly defines a proximal assembly area 14 at the tip 5 and a housing area 15 of said internal part 8.

The area 14 has a shape complementary to that of the tip 5, enabling assembly of the sprayer body 6 to the tip 5 by fitting and locking.

The housing area 15 is divided successively, in the proximal-distal direction, into a first cylindrical part 15a, a groove 15b, a conical part 15c and a second cylindrical part 15d, adapted to receive the corresponding parts of the internal part 8 as will be described below.

The transverse wall 10 forms a conduit for delivering the product, comprising successively, in the proximal-distal direction, grooves arranged in the proximal surface of the wall 10, a cylindrical chamber and the spraying aperture 11. The grooves are arranged so as to open more or less tangentially into said chamber, so as to generate a swirling flow of the product to be sprayed, and the diameter of the aperture 11 is smaller than that of this chamber, such that spraying of the product is caused upon flow of this product from said chamber toward the aperture 11. A spray conduit structure of this type itself is known and therefore will not be described in further detail.

The wall 10 also forms, at the level of its distal surface, a recess for receiving a sealant buffer 22 integral with the cap 7.

The latter part is also bush-shaped, comprising an open proximal end and a distal end closed by a wall 20, and inwardly defines a cavity for receiving the sprayer body 6. This cap 7 can also be made in particular in polypropylene.

At its proximal end, the cap 6 comprises a edge 21 protruding inwardly, defining a shoulder oriented from the distal side and forming a conical proximal inlet. As appears in FIG. 2, the body 6 has a length such that, when its distal wall 10 bears against the wall 20 of the cap 7, the edge 21 locks behind the shoulder 13 formed by the flange 12. In this assembled position, the cap 7 and the sprayer body 6 are assembly to one another, forming a single assembly, with a limited mobility of the cap 7 in relation to the sprayer body 6.

The wall 20 comprises the sealant buffer 22, covering the spraying aperture 11 in this assembled position. Outside this sealant buffer 22, it has a conical shape, enabling centring and wedging of the sprayer body 6 in the cap 7.

Figure 4:
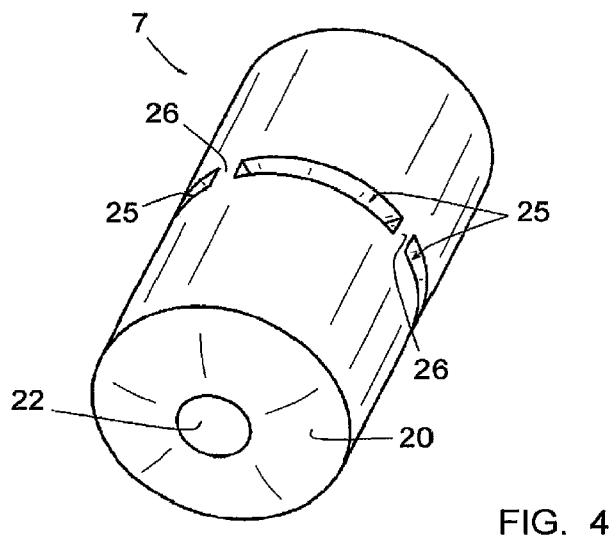
FIG. 4 is a perspective view of this part forming a protective cap, after removal of said separable part.

The cap 7 also comprises, as shown more particularly by FIGS. 2 and 4, a plurality of radial openings 25 going through its wall, arranged substantially halfway from its ends. These openings 25 thus define, on either side of them, a proximal part of the cap 7, designed to be fixed to the container 2, and a distal part of this cap 7, forming the aforementioned separable part. The openings 25 define, between them, material bridges 26 having reduced cross-sections, which can be broken by exerting a transverse or rotational force on the distal part of the cap 7. FIG. 2 shows that a space exists between the sprayer body 6, due to the slightly conical shape of the body 6, and the cylindrical wall of the cap 7, which makes it possible to exert said force so as to break these bridges. The conical shape of the wall 20 also makes it possible, when the distal part of the cap 7 is moved radially in relation to the sprayer body 6 under the exertion of said force, to generate axial stress on the bridges 26, causing them to break.

Figure 5:
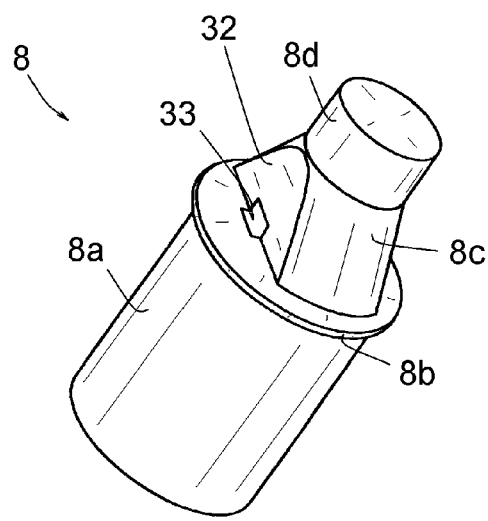
FIGS. 5 and 6 are perspective views from two different angles of another part comprised by the sprayer.
Figure 6:
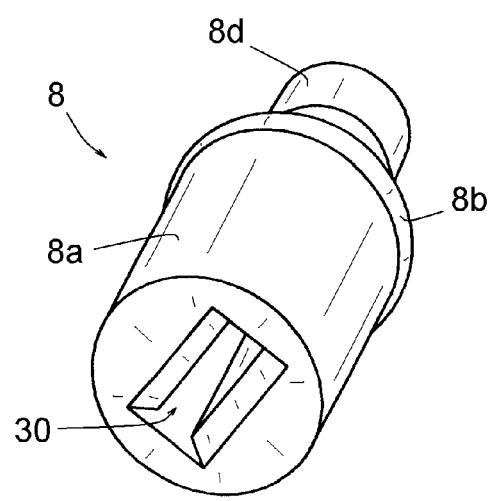

In reference more particularly to FIGS. 5 and 6, the internal part 8 comprises a proximal portion 8a, a peripheral rib 8b arranged at the distal end of this proximal portion 8a, a distal portion 8d and an intermediate portion 8c between this proximal portion 8a and this distal portion 8d.

The proximal portion 8a is dimensioned to be received adjustably in the part 15a of the housing area 15, and defines a proximal internal conduit 30 for the flow of the product to be sprayed.

The rib 8b is designed to be locked in the groove 15b comprised by the sprayer body 6, thereby defining a stable assembly position of the internal part 8 in this body 6.

The distal portion 8d is designed, in the assembled position, to be received in the part 15d of the housing area 15 and to abut against the internal surface of the distal transverse wall 10. It is dimensioned to arrange, between it and the wall defining the part 15d, at least one distal slit 31 for flow of the product to be sprayed.

The portion 8c is a laterally-truncated cone portion, thus defined by two flat walls 32. These walls 32 define, between them and the wall of the body 6 forming said part 15c, two lateral spaces for flow of the product. Two transverse openings 33 are arranged at the area connecting the proximal portion 8a and the intermediate portion 8c, making it possible to connect the conduit 30 and the distal flow slit 31.

The part 8 also has a length such that in the assembled position (cf. FIG. 2), its proximal end comes into the immediate vicinity of the tip 5.

After locking of the edge 21 behind the shoulder 13, the sprayer assembly 3 forms, as mentioned above, a single assembly in which the transverse wall 20 of the cap 7 is in the immediate vicinity of the distal wall 10 of the sprayer body 6, and is formed by parts 6, 7 in a material (polypropylene) having a relative stiffness. This stiffness is such that it enables transmission to the sprayer body 6, through the cap 7, of the force (50 to 100 N) needed for the fitting and locking of this sprayer body 6 on the container 2.

The sprayer assembly 3 can therefore be assembled to the container 2 by just one assembly operation, which thereby makes it possible to decrease the variability of the positioning of the sprayer assembly 3 in relation to the container 2 within a series of sprayers 1.

This decreased variability makes it possible to design the internal part 8 such that its proximal end and its distal end come into the immediate vicinity of the opening of the tip 5 and of the wall 10, respectively. These immediate vicinities also contribute to this reduced variability, the internal part being able to act as a slit when the sprayer assembly 3 is assembled on the container 2. The application of this internal part 8 against the wall 10 also promotes the tightness of the sprayer 1 and moreover makes it possible to reduce the dead volume of product in the flow conduit formed by the sprayer body 3.

The breakable bridges 26 constitute elements making the sprayer tamper-evident, and enable easy implementation thereof. Said proximal part of the cap 7 is, after breaking of the bridges 26, perfectly maintained in relation to the sprayer body 6 by additional engagement surfaces constituted by the shoulder 13, the edge 21 and the shoulder formed by the container 2 between the body 4 and the tip 5.

As appears from the preceding, the invention provides a sprayer, in particular for medical use, presenting determining advantages with respect to similar sprayers of the prior art, in particular:

being able to be assembled in just one assembly operation;
having reduced variability of the positioning of the sprayer assembly 3 in relation to the container 2;
being perfectly tight;
having a reduced dead volume;
having easy implementation and being tamper-evident.

The invention was described above in reference to an embodiment given purely as an example. It goes without saying it is not limited to this embodiment, but that it extends to all the embodiments covered by the appended claims.

The invention claimed is:

1. A sprayer including a container of product to be sprayed, provided with a delivery opening for the product to be sprayed, and a spraying assembly, the spraying assembly being in fluid communication with the delivery opening and being securable onto the container by insertion about a mounting axis, the spraying assembly including a sprayer body delimiting a proximal area conformed to be securable to the container, and including a distal wall, transverse to the mounting axis, in which a spraying aperture is arranged, and a cap including an edge locked on the sprayer body behind a planar surface wherein the planar surface extends perpendicular to a longitudinal axis of the sprayer body, wherein the cap includes a wall transverse to the mounting axis, the wall being sufficiently rigid so as to bear, without substantial damaging, a force from 50 to 100 N necessary to secure the sprayer body to the container and thus to enable the transmission to the sprayer body of the force, wherein the sprayer body and the cap form complementary engaging surfaces, wherein when the complementary engaging surfaces are engaged in an assembly position, axial movement of the cap with respect to the sprayer body is limited, and wherein the cap consists of at least two coaxial parts connected by at least one breakable bridge, wherein one part of said at least two coaxial parts is proximal and is securable to the sprayer body and a second part of said at least two coaxial parts is distal and is displaceable at the moment of use of the sprayer, by rupture of the at least one bridge.

2. The sprayer according to claim 1, wherein the transverse wall of the cap comes, in a mounted position of the cap on the sprayer body, adjacent to the transverse distal wall of the sprayer body so as to eliminate or reduce any play between the cap with respect to the sprayer body.

3. The sprayer according to claim 1, wherein the transverse wall of the cap covers the spraying aperture and includes at least one sealing element at the transverse wall having an area covering the spraying aperture, the at least one sealing element making it possible to sealingly close the spraying aperture.

4. The sprayer according to claim 1, wherein the edge of the cap projects in an inward direction to rest against the planar surface.

5. The sprayer according to claim 4, wherein the sprayer body and the cap are formed so that the edge of the cap can snap beyond the planar surface.

6. The sprayer according to claim 1, wherein at least two coaxial parts are connected to one another by a plurality of breakable bridges, wherein the second part of the at least two coaxial parts is distal and is displaceable at the moment of use of the sprayer, by rupture of the plurality of breakable bridges.

7. The sprayer according to claim 4, wherein:
the container is a syringe body forming a shoulder at a connection area to the delivery opening;
the planar surface of the sprayer body is arranged at a proximal end of the sprayer body;
the inwardly projecting edge of the cap is arranged at a proximal end of the cap; and
a mounted position of the sprayer body is such that in the mounted position of the sprayer body on the delivery opening, the planar surface and the shoulder delimit between them a groove, so that the edge can be received in the groove.

8. The sprayer according to claim 6, wherein the sprayer body and the cap are mutually dimensioned so that there exists, in a mounted position, a space between the sprayer body and the cap, the space being such that it allows the exercise of a transverse or rotational force on a distal part of the cap, making it possible to exert stresses on the breakable bridges in order to help to break the bridges.

9. The sprayer according to claim 6, wherein the transverse wall of the cap has a conical form making it possible, when the cap is moved radially with respect to the spraying body, to generate an axial tension on the breakable bridges.

10. The sprayer according to claim 4, including an internal part placed in a distal chamber which the sprayer body delimits, the internal part having a length such that, in a mounted position, a distal end of the internal part comes adjacent to the transverse distal wall of the sprayer body while a proximal end of the internal part comes adjacent to the delivery opening.

11. The sprayer according to claim 10, wherein the internal part includes:
a proximal portion dimensioned to be received in a part of the chamber intended to receive the proximal portion, the proximal portion delimiting an internal proximal conduit for the flowing of the product to be sprayed;
a distal portion intended, in a mounted position, to come against an internal surface of the transverse distal wall of the sprayer body, and dimensioned to delimit, between the distal portion and a wall of the distal chamber, at least one distal conduit for the flowing of the product to be sprayed; and
an intermediate portion between the proximal portion and the distal portion, in which is arranged at least one transverse opening making it possible to put in communication the internal proximal conduit of the proximal portion and the at least one distal conduit.

12. The sprayer according to claim 10, wherein the sprayer body includes an assembly area and the internal part forms a complementary assembly area intended to cooperate with the assembly area to carry out the assembly of the sprayer body and the internal part.

13. The sprayer according to claim 10, wherein a conduit of flow of the product includes a cylindrical chamber in which emerge tangential conduits to generate a swirling flow of the product to be sprayed, and wherein the cylindrical chamber and/or the tangential conduits are arranged in the transverse distal wall of the sprayer body or in the internal part.

14. A process for making a sprayer according to claim 1, comprising the following steps:
- locking the cap on the sprayer body of the spraying assembly before mounting the sprayer body on the container; and
- exerting the force of from 50-100 N on the wall of the cap so as to enable the mounting of the spraying assembly onto the container.

\* \* \* \* \*